United States Patent
Patton et al.

(10) Patent No.: US 11,509,755 B2
(45) Date of Patent: Nov. 22, 2022

(54) METHOD AND MEANS FOR EVALUATING TORIC CONTACT LENS ROTATIONAL STABILITY

(71) Applicant: Johnson & Johnson Vision Care, Inc., Jacksonville, FL (US)

(72) Inventors: Jaqunda Patton, Jacksonville, FL (US); Ranganath Raja, Jacksonville, FL (US); Peter Sites, Orange Park, FL (US); Benjamin Straker, Jacksonville, FL (US); Raymond Szkutak, Jacksonville, FL (US); Jason Tokarski, Jacksonville, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 314 days.

(21) Appl. No.: 15/851,843

(22) Filed: Dec. 22, 2017

(65) Prior Publication Data
US 2019/0104210 A1    Apr. 4, 2019

Related U.S. Application Data

(60) Provisional application No. 62/565,437, filed on Sep. 29, 2017.

(51) Int. Cl.
*H04M 1/02*    (2006.01)
*G02C 7/04*    (2006.01)
(Continued)

(52) U.S. Cl.
CPC ......... *H04M 1/0264* (2013.01); *A61B 3/0025* (2013.01); *A61B 3/10* (2013.01);
(Continued)

(58) Field of Classification Search
CPC ..... H04M 1/0264; G02B 7/14; G02B 13/001; G02B 15/10; G02C 7/04; G02C 7/021; A61B 3/0025; A61B 3/10
(Continued)

(56) References Cited

U.S. PATENT DOCUMENTS

2007/0273828 A1* 11/2007 Polland ................. G02C 7/021
351/159.69
2015/0351623 A1* 12/2015 Watanabe ............ A61B 3/0041
351/206
(Continued)

FOREIGN PATENT DOCUMENTS

| CA | 2717328 | 4/2012 |
| WO | WO2006135561 | 12/2006 |
| WO | WO2016179370 | 11/2016 |

*Primary Examiner* — Marin Pichler
*Assistant Examiner* — Mitchell T Oestreich

(57) ABSTRACT

The present invention is directed to a method and means for enabling contact lens wearers to photograph their own eyes using an electronic device with a camera such as an iPhone with a macro lens, for example, Olloclip® Macro Pro Lens Set 7× lens, and a custom three-dimensional printed eyecup attachment. The eyecup attachment is designed to position the camera at a suitable and reproducible distance from the eye to ensure that the system can focus appropriately on the lens details. The eyecup attachment also serves to block stray light and diffuse the ambient lighting. In addition, the eyecup attachment ensures that the camera is held in the correct orientation while photos are being captured. The capture images are analyzed using image processing software to determine the angel of rotation of the contact lens.

2 Claims, 4 Drawing Sheets

(51) Int. Cl.
*G02B 15/10* (2006.01)
*G02B 7/14* (2021.01)
*G02B 13/00* (2006.01)
*A61B 3/10* (2006.01)
*G02C 7/02* (2006.01)
*A61B 3/00* (2006.01)

(52) U.S. Cl.
CPC ............ *G02B 7/14* (2013.01); *G02B 13/001* (2013.01); *G02B 15/10* (2013.01); *G02C 7/021* (2013.01); *G02C 7/04* (2013.01)

(58) Field of Classification Search
USPC .......................................................... 359/819
See application file for complete search history.

(56) References Cited

U.S. PATENT DOCUMENTS

2016/0287067 A1* 10/2016 Fan ............................ G06T 7/73
2017/0119250 A1* 5/2017 Kolachalama ....... A61B 3/1208
2018/0299695 A1* 10/2018 Rude ........................ A61B 3/14

* cited by examiner

METHOD AND MEANS FOR EVALUATING TORIC CONTACT LENS ROTATIONAL STABILITY

CROSS REFERENCE TO RELATED APPLICATIONS

This patent application claims the benefit of U.S. Provisional Application No. 62/565,437 filed Sep. 29, 2017.

BACKGROUND OF THE INVENTION

1. Field of the Invention

The present invention is directed to a method for evaluating the rotational stability of toric contact lenses on eye, and more particularly to a method enabling contact lens wearers to photograph their own eyes using an electronic device having a camera with a macro lens and a custom three-dimensional printed eyecup attachment.

2. Discussion of the Related Art

Myopia or nearsightedness is an optical or refractive defect of the eye wherein rays of light from an image focus to a point before they reach the retina. Myopia generally occurs because the eyeball or globe is too long or the dome of the cornea is too steep. A minus powered spherical lens may be utilized to correct myopia. Hyperopia or farsightedness is an optical or refractive defect of the eye wherein rays of light from an image focus to a point after they reach or behind the retina. Hyperopia generally occurs because the eyeball or globe is too short or the dome of the cornea is too flat. A plus powered spherical lens may be utilized to correct hyperopia. Astigmatism is an optical or refractive defect in which an individual's vision is blurred due to the inability of the eye to focus a point object into a point image. Astigmatism is caused by an uneven curvature of the cornea or other ocular refracting surfaces whereby the curvature of the refracting surface varies with angular meridian. A non-astigmatic cornea is rotationally symmetrical whereas in an individual with astigmatism, the cornea is not rotationally symmetrical. In other words, the cornea is more curved or steeper in one meridian than another, thereby causing a point object to be focused as two line foci rather than a single point focus. A cylindrical lens rather than a spherical lens may be utilized to resolve astigmatism.

A toric lens is an optical element having two different powers in two principal meridians that are perpendicular to one another. Each principal meridian of the toric lens corrects the refractive error of the eye within the corresponding plane. The powers of the correcting lens along its principal meridians are created with curvatures of the lens surface that are different at each principal meridian. The orientation of the correcting lens, which may be referred to clinically as the cylinder axis, is preferably maintained relative to the eye for optimal vision correction. Toric lenses may be utilized in eyeglasses, intraocular lenses and contact lenses. The toric lenses used in eyeglasses are held fixed relative to the eye thereby always providing optimal vision correction. However, toric contact lenses may tend to rotate on the eye thereby temporarily providing sub-optimal vision correction. Accordingly, toric contact lenses also include a mechanism to keep the contact lens relatively stable on the eye, including if the wearer blinks or gaze direction changes.

It is known that correction of certain optical defects may be accomplished by imparting non-rotationally symmetric corrective characteristics to one or more surfaces of a contact lens such as cylindrical, bifocal, multifocal, wavefront corrective characteristics or decentration of the optical zone. It is also known that certain cosmetic features such as print patterns for treating certain medical conditions, for example problems with the iris or portions thereof, markings and/or fiducials, and the like are required to be placed in a specific orientation relative to the wearer's eye. The use of toric contact lenses is problematic in that the lens must be maintained at a specific orientation while on the eye to be effective. When the contact lens is first placed on-eye, it must automatically position, or auto-position, itself and then maintain that position over time. However, once the contact lens is positioned, it's rotational position tends to fluctuate over time due to the force exerted on the contact lens by the eyelids during blinking and changes in the direction of gaze.

Maintenance of the on-eye orientation of a toric contact lens typically is accomplished by altering the mechanical characteristics of the contact lens. For example, prism stabilization, including tilting of the contact lens' front surface relative to the back surface, thickening of the inferior contact lens periphery, forming depressions or elevations on the contact lens' surface, and truncating the contact lens edge, are all methods that have been utilized to maintain on-eye orientation. Fluctuation in toric contact lens orientation over time directly impacts the quality of vision for astigmatic soft contact lens wearers. Poor vision quality is a key reason for toric lens wearer dropout.

Previous research suggests smaller palpebral aperture, tighter lens fit, lower myopia, and slower reorientation speed correlate with greater toric lens rotational stability.

Current clinical test methods for quantifying rotational instability (stability with blinks, stability with eye versions) are generally not well controlled (e.g., number and frequency of blinks, size and angle of versional eye movements) and may not reflect lens stability in 'real world' conditions.

Accordingly, improved test methods for quantifying toric lens rotational stability under natural wearing conditions would enable more meaningful assessment of lens performance.

SUMMARY OF THE INVENTION

The advantages of the present method and means for evaluating toric contact lens rotational stability overcome the disadvantages associated with current clinical test methods for quantifying rotational stability.

The present invention is directed to a novel test method and device for tracking lens rotation on eye using self-photography, and to characterize the distribution of the resultant data. More specifically, the present invention is directed to a novel method and means for enabling contact lens wearers to photograph their own eyes using an electronic device with a camera such as an iPhone with a macro lens, for example, Olloclip® Macro Pro Lens Set 7× lens, and a custom three-dimensional printed eyecup attachment. The eyecup attachment is designed to position the camera at a suitable and reproducible distance from the eye to ensure that the system can focus appropriately on the lens details. The eyecup attachment also serves to block stray light and diffuse the ambient lighting. In addition, the eyecup attachment ensures that the camera is held in the correct orientation while photos are being captured.

The method and means for evaluating toric contact lens rotational stability provides an easy to utilize and inexpensive way of ensuring desired rotational stability of contact lenses. With this device, there is no need for the patient to travel to the eye care professional. In addition, highly accurate results may be achieved.

BRIEF DESCRIPTION OF THE DRAWINGS

The foregoing and other features and advantages of the invention will be apparent from the following, more particular description of preferred embodiments of the invention, as illustrated in the accompanying drawings.

DETAILED DESCRIPTION OF THE PREFERRED EMBODIMENTS

Figure 1:
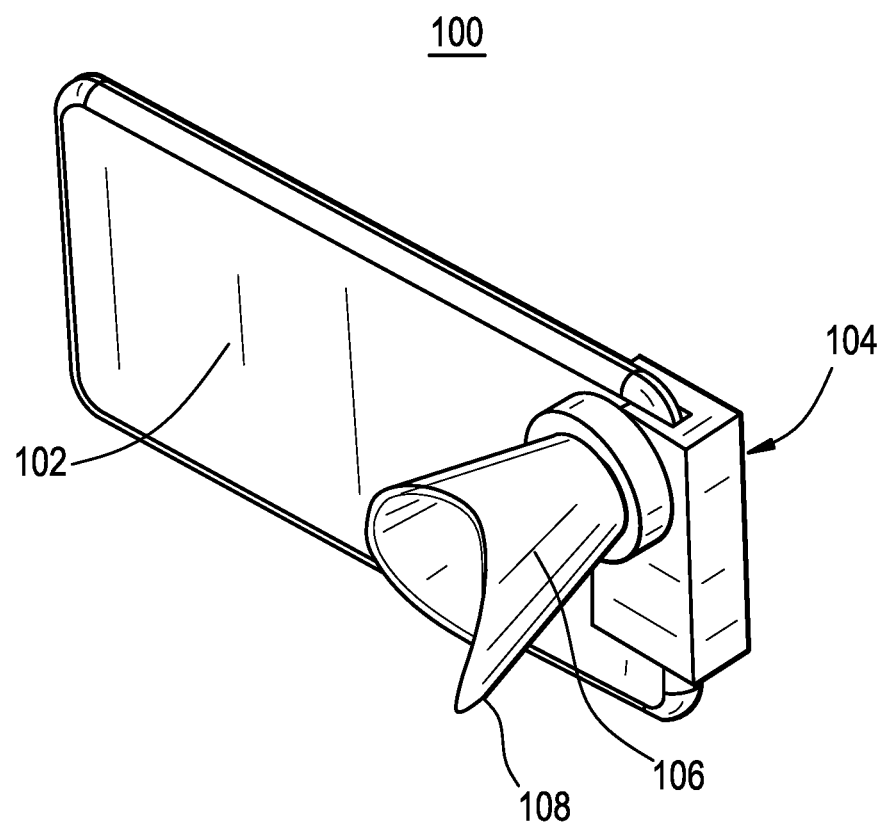
FIG. 1 is a diagrammatic representation of an exemplary electronic device having a camera, a macro lens and eyecup attachment in accordance with the present invention.

Contact lenses or contacts are simply lenses placed on the eye. Contact lenses are considered medical devices and may be worn to correct vision and/or for cosmetic or other therapeutic reasons. Contact lenses have been utilized commercially to improve vision since the 1950s. Early contact lenses were made or fabricated from hard materials, were relatively expensive and fragile. In addition, these early contact lenses were fabricated from materials that did not allow sufficient oxygen transmission through the contact lens to the conjunctiva and cornea which potentially could cause a number of adverse clinical effects. Although these contact lenses are still utilized, they are not suitable for all patients due to their poor initial comfort. Later developments in the field gave rise to soft contact lenses, based upon hydrogels, which are extremely popular and widely utilized today. Specifically, silicone hydrogel contact lenses that are available today combine the benefit of silicone, which has extremely high oxygen permeability, with the proven comfort and clinical performance of hydrogels. Essentially, these silicone hydrogel based contact lenses have higher oxygen permeabilities and are generally more comfortable to wear than the contact lenses made of the earlier hard materials. The design of the contact lenses and the material choice of silicone hydrogel result in a very comfortable interaction of the lenses to that of the wearer's eyelids.

Currently available contact lenses remain a cost-effective means for vision correction. The thin plastic lenses fit over the cornea of the eye to correct vision defects, including myopia or nearsightedness, hyperopia or farsightedness, astigmatism, and presbyopia i.e. the loss of the ability of the crystalline lens to accommodate. Contact lenses are available in a variety of forms and are made of a variety of materials to provide different functionality. Soft contact lenses are typically made from soft polymer materials combined with water. Daily wear soft contact lenses may be daily disposable, reusable or extended wear. Daily disposable contact lenses are usually worn for a single day and then thrown away, reusable disposable lenses are usually reworn over multiple days, and extended wear disposable contact lenses are usually worn for a period of up to thirty days. Colored soft contact lenses use different materials to provide different functionality. For example, a visibility tint contact lens uses a light tint to aid the wearer in locating a dropped contact lens, enhancement tint contact lenses have a translucent tint that is meant to enhance one's natural eye color, the color tint contact lens comprises a darker, opaque tint meant to change one's eye color, and the light filtering tint contact lens functions to enhance certain colors while muting others. Rigid gas permeable hard contact lenses are made from siloxane-containing polymers but are more rigid than soft contact lenses and thus hold their shape and are more durable. Bifocal contact lenses are designed specifically for patients with presbyopia and are available in both soft and rigid varieties. Toric contact lenses are designed specifically for patients with astigmatism and are also available in both soft and rigid varieties. Combination lenses combining different aspects of the above are also available, for example, hybrid contact lenses.

In accordance with the present invention, a study was designed to evaluate a novel test method for tracking lens rotation using self-photography, and to characterize the distribution of the resultant data. The results of the study demonstrate that it is feasible to quantify the stability of a toric contact lens under real-world conditions. It is important to note that in addition to rotational stability; lens movement may be investigated during various activities or eye movements and/or to quantitatively compare the performance of alternate contact lens designs. The study utilized the same system and methodology that is to be utilized by patients and eye care professionals. A detailed description of the study is given subsequent to a detailed description of the system.

As set forth above, the present invention is directed to a method and means for enabling contact lens wearers to photograph their own eyes using a hand-held electronic device having a camera, a macro lens, and an eyecup attachment. FIG. 1 illustrates the system 100 comprising the electronic device 102, the macro lens 104 and the eyecup attachment 106.

The hand-held electronic device 102 comprising a camera may be any suitable device currently available for capturing images with sufficient resolution as set forth below. Examples of hand-held electronic devices with cameras include phones, smart phones, for example, iPhones, tablet computing devices, for example, iPads, high definition webcam, as well as digital cameras and video cameras with wireless and/or Bluetooth connectivity, all with at least a camera option for capturing still images and or video. In an exemplary embodiment in accordance with the present invention, the hand-held electronic device 102 comprises an iPhone, and more specifically an iPhone 6 Plus, although in alternative exemplary embodiments, other smartphone brands and mobile devices may be utilized as set forth above.

A macro lens, in its most general terms, is an optical device that is able to reproduce a life-sized image of an object on a recording medium. True macro lenses provide a magnification factor of 1.0× or 1:1 at its closest focus setting. Essentially, macro lenses can provide massive enlargements of small objects. Any suitable macro lens 104 may be utilized with the present invention and is preferably easy to connect to the camera and is lightweight. In the present invention, a Olloclip® Macro Pro Lens Set 7× lens 104 is utilized with the iPhone 6 Plus 102. This macro lens essentially converts the iPhone into a digital microscope or loupe with edge-to-edge clarity. The Olloclip® Macro Pro Lens Set 7× lens 104 comes with all the necessary components for attachment to the iPhone 102.

The eyecup attachment or eyepiece 106 is designed to position the camera of the electronic device 102 at a suitable distance from the user's eye to ensure that the camera can focus appropriately on the lens details, block stray light and diffuse ambient light and ensure that the camera is held in correct orientation while images are captured. Each image should preferably be from the same vantage point and thus the eyepiece 106 is required to maintain distance and orientation. The eyepiece 106 comprises a wing shaped element 108 that facilitates correct orientation by the user. The eyepiece 106 is preferably manufactured from a lightweight material, for example, a polymer or lightweight metal such as aluminum and may be manufactured by any type of process, including, machining, injection molding and various forms of three-dimensional printing processes. In the exemplary embodiment in accordance with the present invention, the eyepiece 106 is manufactured from a plastic material utilizing a three-dimensional printing process and smoothed sufficiently for placement in contact with the sensitive skin surrounding the eye. In other words, the eyepiece 106 should preferably promote a favorable tactile response. In the exemplary embodiment, the eyepiece 106 has a threaded section for attachment to the lens 104; however, any suitable attachment means may be utilized.

A contact lens with fiducial markings is photographed using the system 100 illustrated in FIG. 1. A detailed description of the contact lens and process is given below in the description of the study. Current clinical methods of measuring toric soft contact lens rotational stability are short in duration, subject to variability and may not reflect real-world performance. The study set forth below investigated the feasibility of a method for quantifying the stability of a toric contact lens under real-world conditions via self-photography. The study's contact lens parameters are given in Table 1 below.

TABLE 1

| Specification | Parameter |
|---|---|
| Material | Senofilcon A |
| Water content (%) | 38 |
| Base curve (mm) | 8.6 |
| Diameter (mm) | 14.3 |
| Lens power (D) | 0.00 (plano) |
| Stabilization design | Blink Stabilized Design (BSD) |

Figure 2:
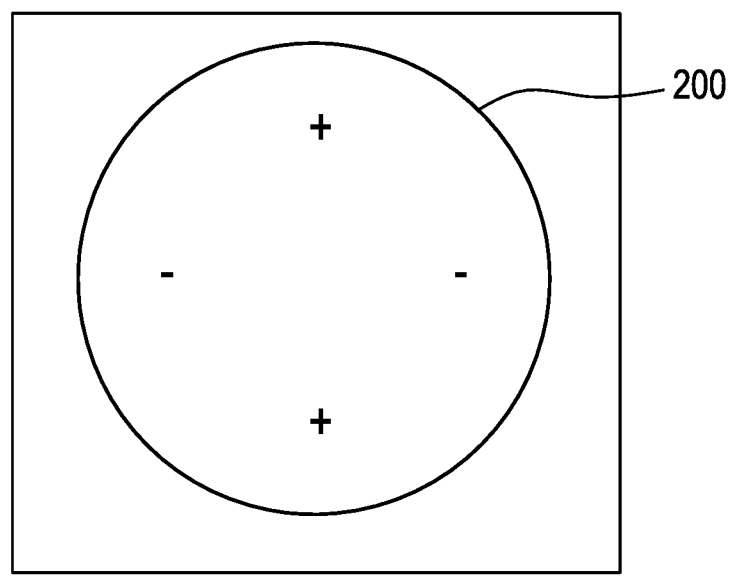
FIG. 2 is a diagrammatic representation of an exemplary contact lens with a fiducial marking scheme in accordance with the present invention.
Figure 3:
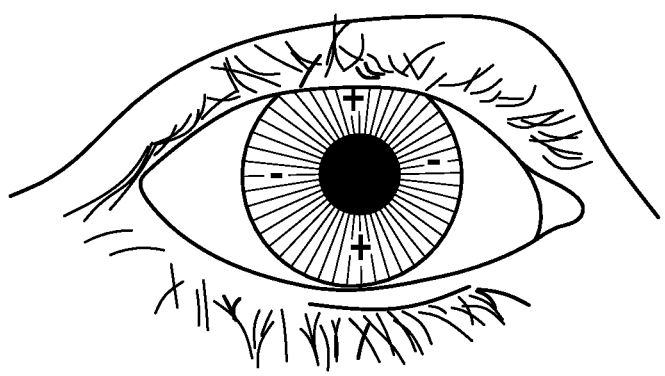
FIG. 3 is an image of the exemplary contact lens with a fiducial marking scheme on eye taken with an exemplary electronic device having a camera, a macro lens and eyecup attachment in accordance with the present invention.

Study lenses featured the same stabilization design used in ACUVUE OASYS® 1-Day for ASTIGMATISM brand contact lenses available from Johnson & Johnson Vision Care and were manufactured with a white fiducial print pattern as illustrated in FIG. 2. The study contact lens 200 comprises two + sign fiducials positioned at 90 and 270 degrees and two − sign fiducials positioned at 0 and 180 degrees. An example image of the study contact lens design captured using the system 100 of FIG. 1 is illustrated in FIG. 3. As may be readily seen, three out of four of the fiducials are clearly seen.

Twelve (12) healthy habitual soft contact lens wearers, twenty-four (24) eyes, between nineteen (19) and thirty-five (35) years of age were enrolled in the study. Subjects were given detailed training and instructions for capturing images in primary position and to review each image immediately following capture to ensure acceptable quality. A timing app 'Timer+' was used to sound an alarm at thirty (30) minute intervals to signal a new capture session. That is, every thirty (30) minutes, an alarm sounded to remind the patient to collect images of both eyes using the device. Subjects wore lenses bilaterally and were instructed to capture a minimum of two (2) images per eye, per capture session over a wear period of at least six (6) hours using the system 100 of FIG. 1. Following completion of the wear period, images were transferred from the iPhone to a computer using a standard USB connector. Images were then analyzed by a trained investigator using custom image processing software application written in MATLAB (The MathWorks, Inc). For each photograph, the image processing software was used to identify the position of certain features within that photograph, including the horizontal lens fiducials (depicted by a − sign) and the ocular canthi. The software used the identified location of these features to calculate the angle of the fiducials with respect to the intercanthal angle.

Figure 4:
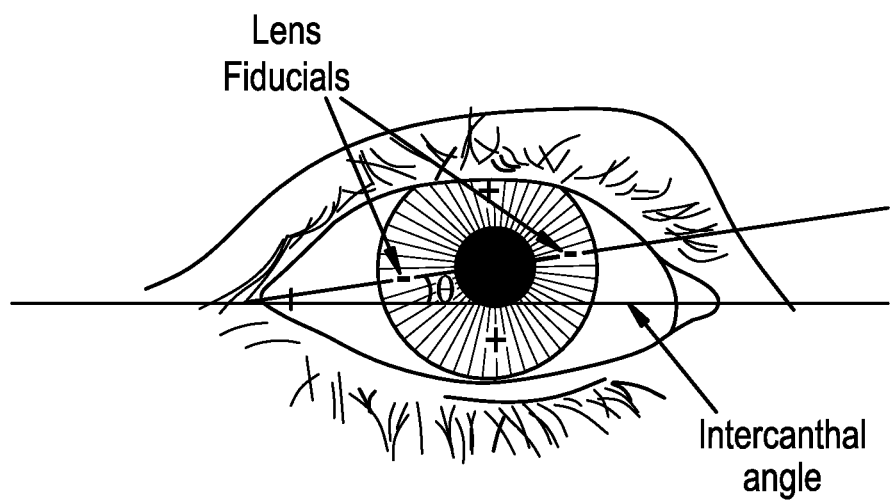
FIG. 4 is an image of the exemplary contact lens with a fiducial marking scheme on eye illustrating the calculation of lens angle relative to a reference line in accordance with the present invention.

For each eye, the first acceptable image of each session was analyzed. Images were considered acceptable if both canthi were within the frame, the image was in focus and exposed well enough that lens fiducials and canthi were visible, and the eye was fixated toward the camera. Images were analyzed to determine the angle of lens rotation θ, defined as the angle of the 0 and 180 degree − sign fiducials relative to the intercanthal angle as illustrated in FIG. 4.

An exploratory analysis was conducted to characterize the distribution of relative lens rotation data. Both eyes of one subject were excluded from the analysis due to poor quality photographs (under-exposure, poor focus, variable fixation). In total, two-hundred seventy-three (273) images from eleven (11) subjects or twenty-two (22) eyes were analyzed. Subject demographics are summarized in Table 2 below.

TABLE 2

| Gender | Male | 7 |
|---|---|---|
|  | Female | 4 |
| Race | Asian | 4 |
|  | African American | 1 |
|  | White | 6 |
| Age | (Mean ± SD) | 26.5 ± 4.6 |
| Mean spherical refraction | (Mean ± SD) | −3.2 ± 1.1 |

Figure 5:
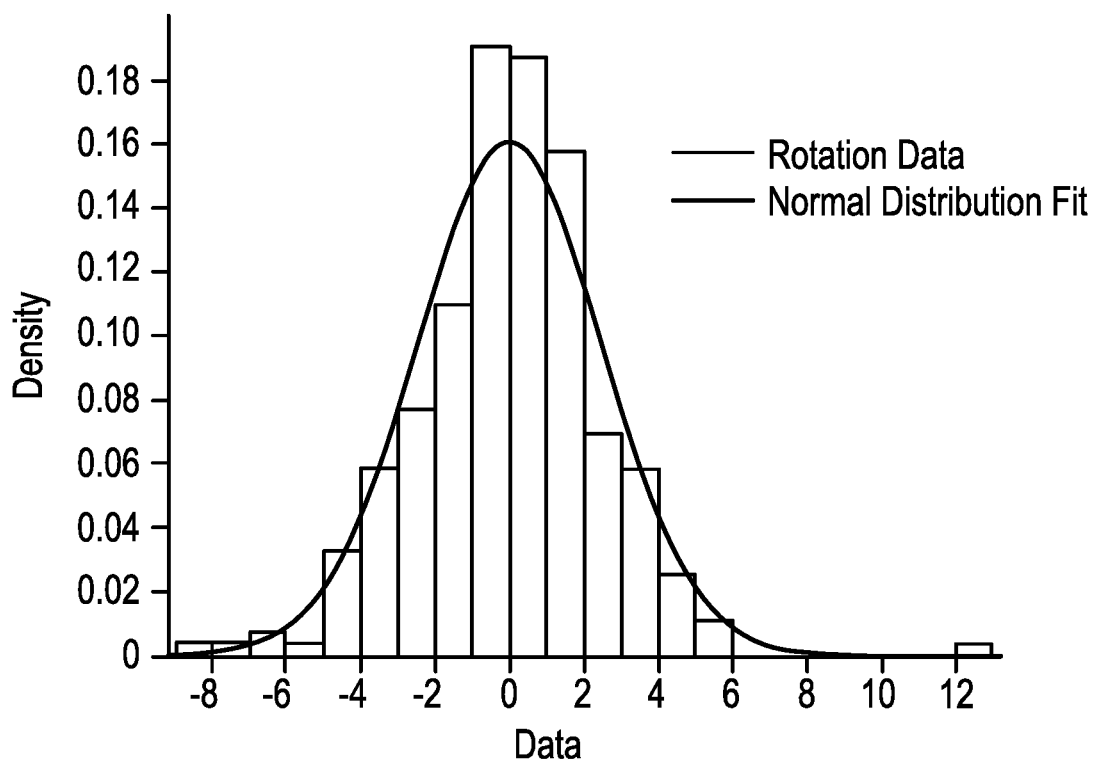
FIG. 5 illustrates the distribution of relative lens rotation over the course of a sample evaluation in accordance with the present invention.

For each eye, the total number of capture sessions range from eleven (11) to fourteen (14) with a median of twelve (12). A histogram of relative lens rotation data for all eyes combined suggested that these data are normally distributed, as illustrated in FIG. 5.

Figure 6:
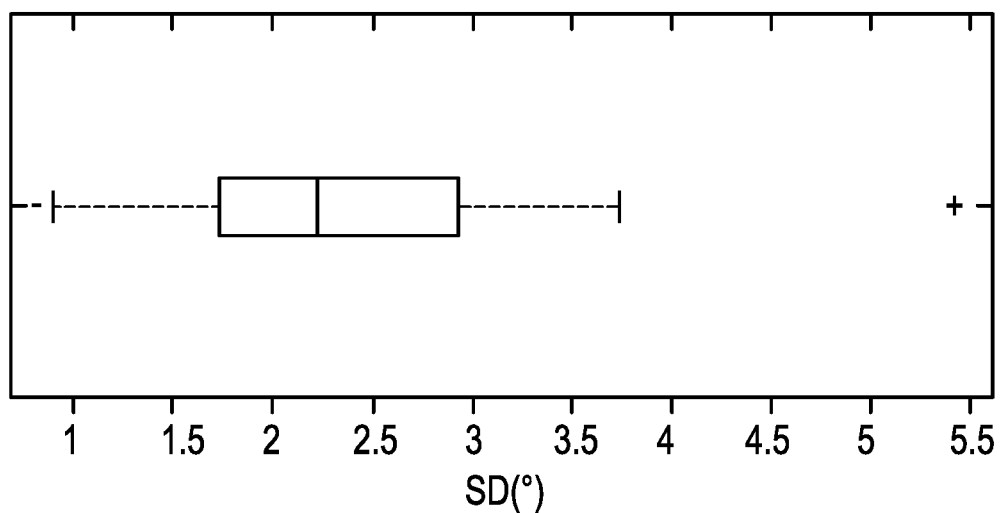
FIG. 6 illustrates a boxplot of standard deviation of lens rotation data by eye in accordance with the present invention.

For each eye, the variability in lens orientation over time was quantified by calculating the standard deviation (SD) of lens rotation data points for that eye. A boxplot of SDs for all eyes included in the analysis is illustrated in FIG. 6. This SD ranged from 0.9 degrees to 5.4 degrees, with a mean standard deviation of 2.4 degree (median 2.2 degrees).

The successful acquisition and analysis of photographs in this study supports the feasibility of this novel test method for evaluating toric lens rotational stability. In addition, the data suggests that the fluctuation in toric lens orientation for this design follows a normal distribution. Given the mean standard deviation of 2.4 degrees, it can be inferred that, for an average eye wearing the toric design used in this study, ninety-five (95) percent of the time the lens was within approximately ±5 degrees (2×SD) of its mean rotational position.

Rotational stability is likely to be dependent on the activities or tasks that the wearer is performing and the physiological state of the eye.

It is important to note that one lens may be utilized as a benchmark to compare one lens against another. More specifically, images of a first contact lens may be analyzed to determine the angle of the first contact lens with the visible fiducial marking relative to a reference line connecting, for example, the nasal and temporal canthi to calculate and characterize the distribution of contact lens rotation data over a predetermined or extended time period. This distribution of the first contact lens may be utilized as the benchmark. The process may be repeated with a second contact lens and the results compared to the benchmark.

A potential limitation associated with this study was that it measured lens orientation relative to intercanthal angle which does not account for cyclotorsion of the globe; this could be addressed in future studies by using more sophisticated image analysis using, for example, conjunctival blood vessels or iris features as landmarks. In addition, future investigations could use this method to investigate toric lens stability during different activities or to compare the relative stability of alternative stabilization designs.

Results of this study; however, support the feasibility of using a device with a digital camera with a macro lens and eyecup with custom printed toric lenses to evaluate toric lens stability during natural wear conditions.

The eyelid stabilized design used in the study lenses demonstrated good rotational stability throughout a six (6) hour wear period.

Although shown and described in what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. A method for evaluating toric contact lens rotational stability on-eye, the method comprising the steps of:
    providing lens wearers with an electronic device including a camera having a macro lens and eyecup attachment that facilitates correct and reproducible orientation of said camera relative to said lens wearers, and at least a first contact lens with visible fiducial markers, wherein the eyecup attachment has a first end attached to said macro lens, and an opposing free second end defined by a three-dimensional, non-planar, asymmetric peripheral edge having a shape adapted for placement in contact with skin surrounding an eye of said lens wearers, said peripheral edge includes a first portion that is planar and a second portion that is non-planar and projects outwardly away from the plane of the first portion in a direction away from said first end of said eyecup, wherein said second portion enables repeatable distance and angular orientation of the camera relative to said eye of said lens wearers;
    instructing lens wearers to properly orient said camera using said eyecup attachment;
    instructing lens wearers to photograph each eye while wearing their contact lens at fixed time intervals over an extended time period and while engaged in different activities and tasks using the electronic device with said camera properly oriented each time; and
    analyzing photographs of the contact lens on-eye using image processing software to determine the angle of the first contact lens with visible fiducial markers relative to a reference line connecting the nasal and temporal canthi to calculate and characterize the distribution of contact lens rotation data over the extended time period.

2. The method of claim 1 further comprising the steps of:
    using the calculated and characterized distribution of contact lens rotation data over the extended time period as a reference benchmark;
    providing lens wearers with a second contact lens different from the first contact lens, the second contact lens including visible fiducial markers;
    instructing lens wearers to photograph each eye while wearing the second contact lens at fixed time intervals over an extended time period and while engaged in different activities and tasks using the electronic device with said camera oriented in substantially the same manner as in the first photographing step each time;
    analyzing photographs using image processing software to determine the angle of the second contact lens with visible fiducial markers relative to a reference line connecting the nasal and temporal canthi to calculate and characterize the distribution of contact lens rotation data over the extended time period; and
    comparing the calculated and characterized contact lens rotation data of the second contact lens with that of the first contact lens which serves as a reference benchmark.

* * * * *